(12) United States Patent
Prince et al.

(10) Patent No.: US 7,789,601 B2
(45) Date of Patent: Sep. 7, 2010

(54) MILL BLANK MANDREL

(75) Inventors: Jeffrey Prince, Grass Valley, CA (US);
Rod Duncan, Plano, TX (US); Branko Bem, Plano, TX (US)

(73) Assignee: D4D Technologies, LLC, Richardson, TX (US)

( * ) Notice: Subject to any disclaimer, the term of this patent is extended or adjusted under 35 U.S.C. 154(b) by 792 days.

(21) Appl. No.: 10/867,342

(22) Filed: Jun. 14, 2004

(65) Prior Publication Data

US 2005/0276672 A1 Dec. 15, 2005

(51) Int. Cl.
*B23Q 3/00* (2006.01)
(52) U.S. Cl. ............... 409/219; 409/220; 409/225; 279/77; 279/97; 433/49; 433/223; 428/542.8; 269/287; 403/323; 403/379.4
(58) Field of Classification Search ........... 409/219, 409/220, 225; 433/49, 223; 428/542.8; 269/287, 269/6, 3, 47; 403/323, 379.4, 379.5; 279/79, 279/97, 77, 81, 76, 86
See application file for complete search history.

(56) References Cited

U.S. PATENT DOCUMENTS

| | | | | |
|---|---|---|---|---|
| 2,781,199 A | * | 2/1957 | Veldhuizen | 279/77 |
| 2,816,770 A | * | 12/1957 | De Vlieg et al. | 279/97 |
| 4,615,678 A | * | 10/1986 | Moermann et al. | 433/201.1 |
| 5,114,264 A | * | 5/1992 | Barlow | 403/323 |
| 5,135,393 A | * | 8/1992 | Eidenbenz et al. | 433/53 |
| 5,342,696 A | * | 8/1994 | Eidenbenz et al. | 433/49 |
| 5,380,117 A | * | 1/1995 | Buschulte | 403/323 |
| 6,506,838 B1 | * | 1/2003 | Seyama | 525/154 |
| 2003/0031984 A1 | * | 2/2003 | Rusin et al. | 433/215 |
| 2003/0073394 A1 | * | 4/2003 | Reidt et al. | 451/398 |
| 2006/0035775 A1 | * | 2/2006 | Duncan et al. | 409/96 |
| 2007/0050072 A1 | * | 3/2007 | Schwotzer | 700/116 |
| 2008/0117021 A1 | * | 5/2008 | Brunski | 340/5.81 |

FOREIGN PATENT DOCUMENTS

| | | | |
|---|---|---|---|
| CA | 2322761 A1 | * | 9/1999 |
| DE | 9204892 U1 | | 6/1993 |
| DE | 19733161 A1 | * | 2/1999 |
| EP | 455854 A1 | * | 11/1991 |
| SU | 427361 A | * | 11/1974 |
| WO | WO-01/50407 A1 | * | 7/2001 |
| WO | WO-2008/083358 A1 | * | 7/2008 |

OTHER PUBLICATIONS

Machine Translation of DE-19733161, 6 pages.*
Machine Translation of DE 9204892-U1, 4 pages.*

* cited by examiner

*Primary Examiner*—Erica E Cadugan
(74) *Attorney, Agent, or Firm*—Haynes and Boone LLP

(57) ABSTRACT

A mill blank mandrel may rigidly secure machinable material for a machining process. The mandrel may be freely and easily inserted in a corresponding mandrel socket and secured without the use of a tool. The mandrel may be detected and verified when inserted in the mandrel socket.

21 Claims, 17 Drawing Sheets

MILL BLANK MANDREL

BACKGROUND OF THE INVENTION

1. Related Field

The invention relates to a mill blank mandrel, and in particular to mandrels for preparing dental restorations such as crowns, inlays, onlays, copings, frameworks, bridges, implants or other dental prostheses.

2. Description of the Related Art

Dental prostheses may be formed or manufactured as a replacement for or an improvement for tooth structure that may be broken, damaged, decayed, missing or otherwise in a state of disrepair. The tooth structure may be prepared to receive a restoration and a model of the prepared tooth and surrounding dentition and gingival tissues may be made. An interim restoration may be temporarily affixed to the preparation while a final restoration or prosthesis is prepared using the model. The restoration may be prepared by machining, through a lost wax casting process, layering or any other process for preparing a dental prosthesis. The restoration may be milled from a block of material suitable for a dental application. The block may be secured or rigidly fixed so that cutting tools of a milling machine may engage the block to form the shape of the restoration. The restoration may be finished for a proper fit for the application and rigidly fixed or seated to the preparation.

SUMMARY OF THE INVENTION

The embodiments provide a dental mill blank mandrel and a mandrel socket that provides a quick-change means for securing a dental mill blank for machining processes. Embodiments include apparatuses, methods, processes, systems, and techniques for freely and quickly securing a dental blank for a machining process.

A mill blank mandrel may secure a block of material such as a dental blank for a machining process. The mill blank mandrel may include a block of machinable material affixed to a mounting spud. The block of material may have a general shape, configuration and arrangement for a desired application. For example, the blank may have a general shape for a dental crown for an adult male. The block of material may be secured to the mounting spud by adhesive bonding, soldering, mechanical staking or any combination thereof. The block of material may be referred to as a dental blank.

The mounting spud may include a shoulder and an elongated body or shaft. The shoulder may have an outer circumference that is larger than an outer circumference of the shaft. The shaft may have a linear cross-section over the length of the shaft. The shaft also may have a nonlinear cross-section over at least a portion of the length of the shaft. The non-linear cross-section may provide a moment bearing surface with respect to a longitudinal axis of the shaft. The non-linear cross-section may preclude axial rotation of the shaft when a force is applied to the surface of the shaft. For example, the shaft may have a generally circular cross-section with a keyway or planar surface through at least a portion of the shaft. A force applied to the keyway may prevent rotation of the shaft about the longitudinal axis of the shaft. The keyway may have a cylindrical or prismatic shape at a predetermined distance from the shoulder. The keyway or planar surface may be located at a predetermined distance from the shoulder. The keyway may also have a predetermined angle with respect to a longitudinal axis.

The mill blank mandrel may be secured by a mandrel socket. The shaft may be inserted into and rigidly fixed within the mandrel socket. The mandrel socket may have face defining an opening to a cavity. The opening and cavity may have a cross-section corresponding to the cross-section of the shaft. The cavity may have a depth sufficient to allow the shaft to be inserted into the cavity to the shoulder. The shoulder may provide a stop for the shaft when it is inserted into the cavity. The depth of the cavity may also be sufficient to allow the shaft to be inserted to a desired depth, so that the shaft rest against a bottom or end of the cavity when the shaft is inserted in the cavity.

The mandrel socket may also have a keyhole. The keyhole may be a cylindrical or prismatic hole at an angle with respect to a longitudinal axis of the cavity. The angle of keyhole may correspond to the orientation of the keyway of the shaft. The keyhole may be positioned a distance from the opening that corresponds to the distance of the keyway on the shaft from the shoulder. The keyhole may also be positioned a distance from the opening that corresponds to the distance of the keyway on the shaft from an end of the shaft. When the elongated body is inserted into the cavity, the keyhole and keyway may align to form a contiguous aperture. A pin or key may be positioned in the aperture, securing the mounting spud to the mandrel socket. The pin may be manipulated to secure or lock the spud within the mandrel socket.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE INVENTION

A mill blank mandrel may rigidly secure a machinable material such as a mill blank. The mill blank may have a general shape, configuration and arrangement for a particular application. The mill blank mandrel easily and securely fastens the machinable material for a machining process.

The mill blank mandrel may be inserted into a mandrel socket. The mandrel socket may rigidly secure the mill blank mandrel, and thereby rigidly secure the machinable material. The mill blank mandrel also may be freely and easily removed from the mandrel socket. This mill blank mandrel and the mandrel socket rigidly fix the machinable material while machining operations may be performed on the material. The mill blank mandrel may restrict rotational and lateral motion of the machinable material with respect to cutting tools, drill bits, burs and other machining tools.

Figure 1:
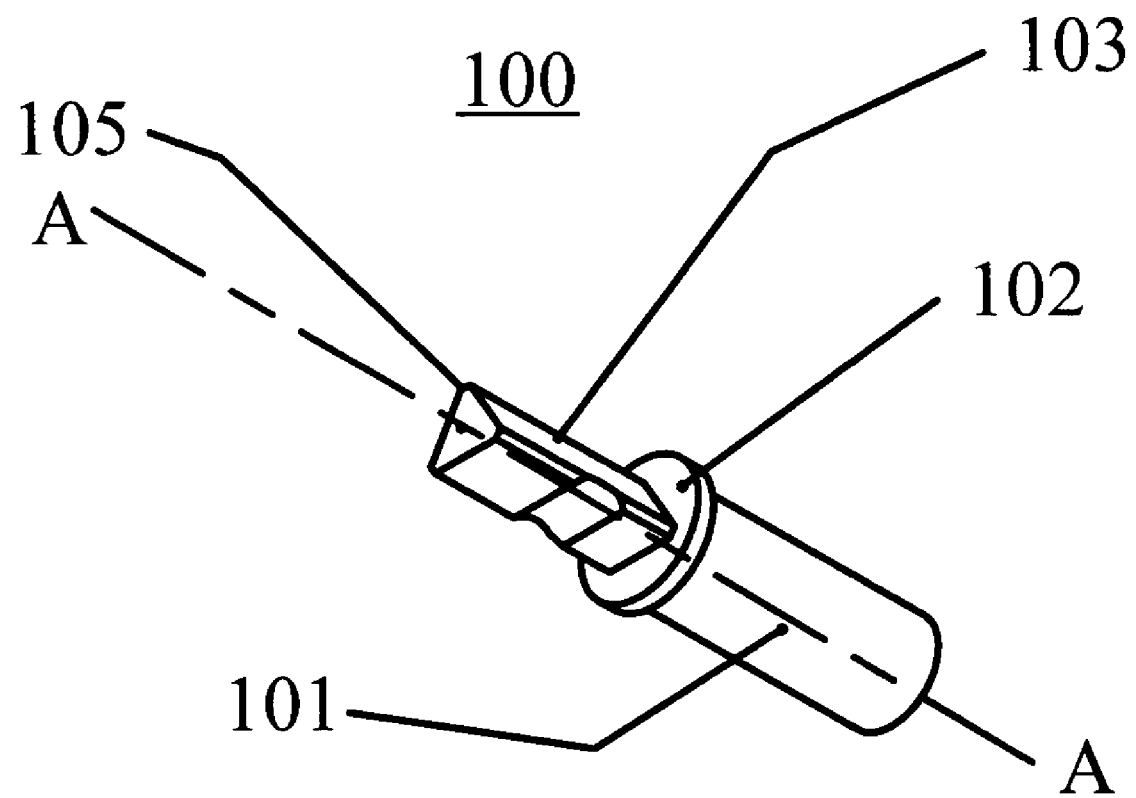
FIG. 1 illustrates mill blank mandrel having longitudinal axis A-A.

FIG. 1 illustrates an example of a mill blank mandrel 100. The mill blank mandrel 100 includes a shoulder 102 and an elongated body 103 or shaft, and a block of machinable material or dental blank. The mill blank 101 may be a unitary part of the mill blank mandrel 100. The mill blank 101 may be any machinable material suitable. The mill blank 101 may be any material that may be formed to a desired shape through a machining process such as through the engagement of cutting dies, gigs, bits, burs, and the like. In embodiment, the mill blank 101 may be any material or combination of materials suitable for dental applications, such as metal, ceramic, porcelain, polymeric material, amalgams, alloys, or any combination thereof. The mill blank may have a general shape for a dental crown, inlay, onlay, coping, framework, bridge, implant or other dental prostheses or restoration.

The mill blank 101 may be mechanically coupled, rigidly fixed, or releasably secured to the mill blank mandrel 100 by any suitable means to secure the mill blank 101 to the mill blank mandrel 100. The mill blank 101 may be coupled by cementing, bonding, mechanically staking, soldering, pressure fit, any combination thereof or any other mechanical coupling system.

The shoulder 102 and the elongated body 103 may be a unitary part. The elongated body 103 and the shoulder 102 also may be mechanically coupled. The shoulder 102 and the elongated body 103 may be a solid material or composite materials such as metals, metal alloys, plastics, ceramics, porcelain, any combination thereof or the like.

The elongated body 103 may be referred to as a mounting spud, a spud shaft, a spud, a mounting shaft, or a shaft. The spud 103 may be characterized by a cross-section centered about a central longitudinal axis A-A of the mill blank mandrel 100. The axis A-A may extend from the shoulder 102 to a face 105 of the spud 103. The cross-section may be linear over the length of the spud 103. The cross-section also may be non-linear over at least a portion of the length of the spud 103.

The cross-section may be any geometric shape. The cross-section may be generally circular, elliptical, or non-circular. In an embodiment, the cross section may be triangular. In another embodiment, the cross section may be square, elliptical, D-Shaped, T-shaped, circular, or semi-circular. The cross-section may be any shape, size, arrangement, or symmetry that provides rotational immobility about axis A-A when a force is applied to at least an outer surface of the spud 103.

The shoulder 102 may have a central axis that is concentric with the central axis A-A. The shoulder 102 may have an outer perimeter or cross-section that is larger than the cross-section of the spud 103. The shoulder 102 may provide a singular insertion distance of the spud 103. The face 105 also may provide a singular insertion distance of the mill blank mandrel spud 103.

Figure 2:
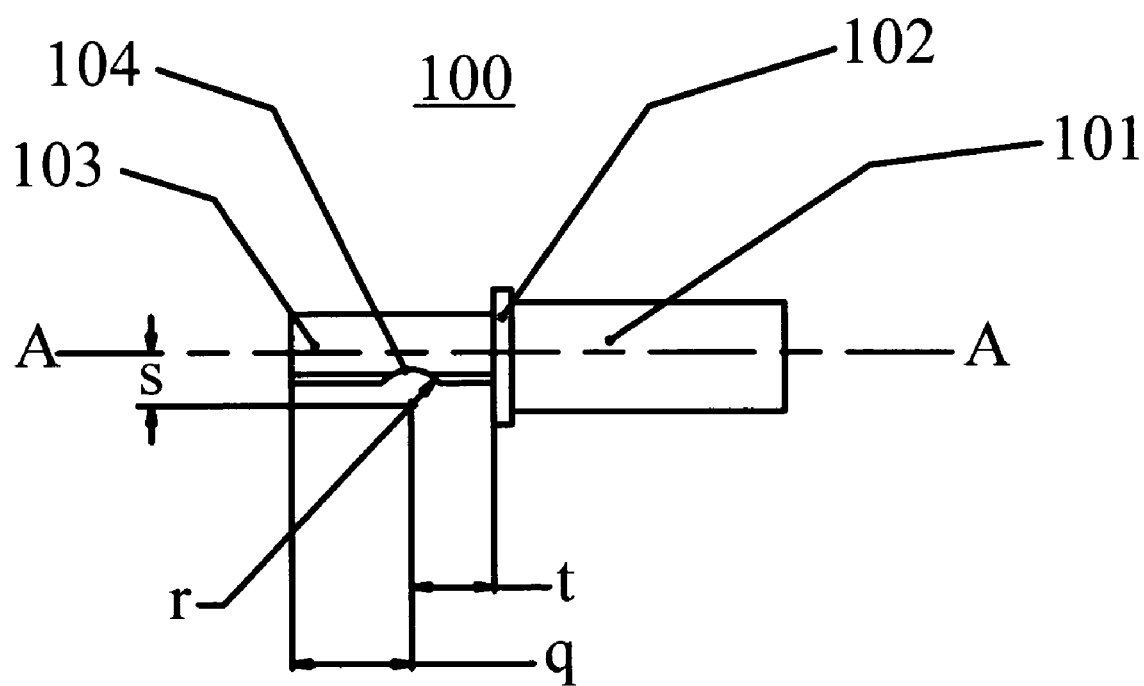
FIG. 2 illustrates a side view of the mill blank mandrel of FIG. 1 having longitudinal axis A-A.
Figure 3:
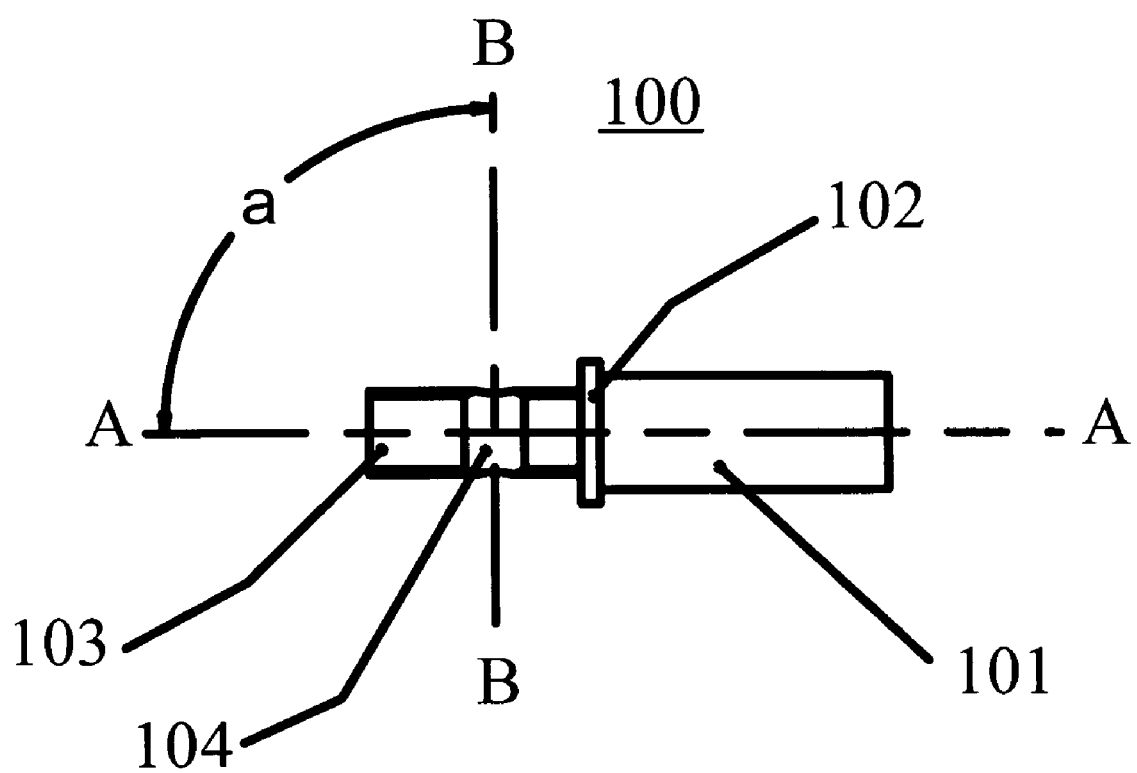
FIG. 3 illustrates a bottom view of the mill blank mandrel of FIG. 1 having a keyway axis B-B.

FIG. 2 illustrates a side view and bottom view of the mill blank mandrel 100 and FIG. 3 illustrates a bottom view of the mill blank mandrel 100. The spud 103 may include a keyway or groove 104. The keyway may be positioned a distance t from the shoulder 102. The keyway 104 also may be positioned a distance q from the face 105. The keyway 104 may have a central axis B-B. The keyway 104 may be centered about a locus by a distance r. The distance r may be positioned a depth s from axis A-A. The keyway may also have a characteristic opening dimension r. The dimensions q, r, s, and t have no bounds other than the keyway must not weaken the shaft in its purpose to secure the block of machinable material.

The axis B-B may be at an angle a with respect to the axis A-A. In an embodiment, the angle a may be 90 degrees where the axis B-B is perpendicular to axis A-A. The angle a may be determined based on the fiction characteristics of the shaft 103 and any other materials with which the shaft 103 may interact. The dimensions q, r, s, t and a may be associated with a position and orientation of the keyhole 104. The keyhole 104 may define a any geometric shape in the shaft 103. For example, the keyhole may be circular, semicircular, or rectangular.

Figure 4:
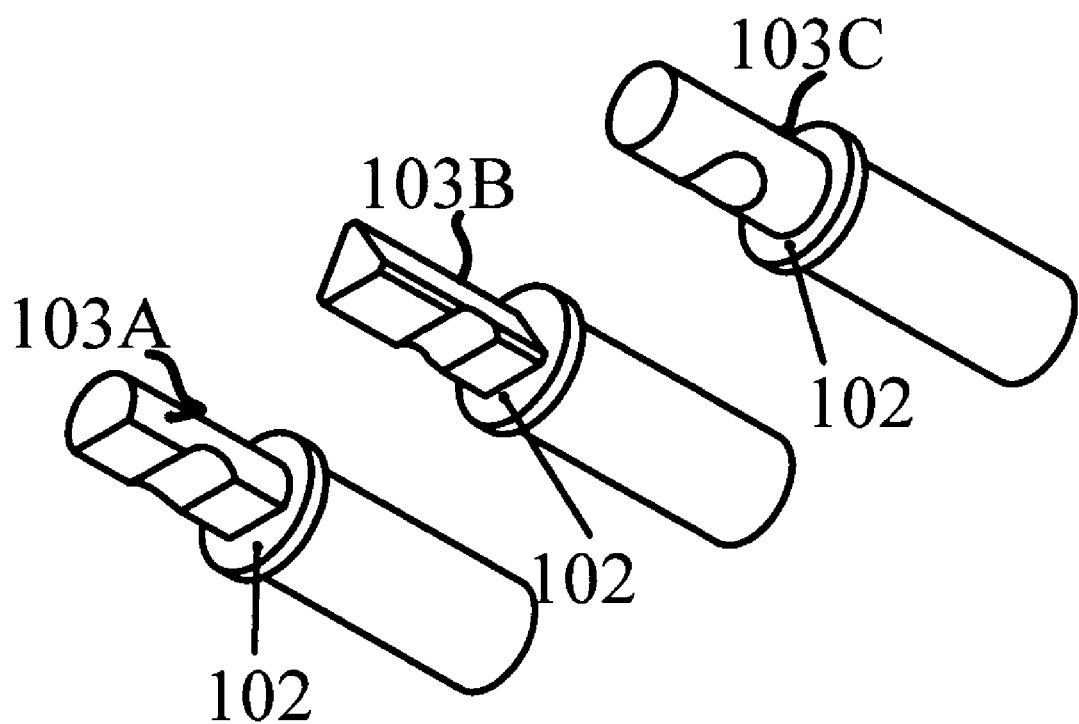
FIG. 4 illustrates exemplary embodiments of the mill blank mandrel of FIG. 1.

FIG. 4 illustrates several embodiments of the mill blank mandrel 100. As shown, the spud 103 may have any desired cross-section along axis A-A. The spud 103 may be D-shaped 103A, triangular 103B, or circular 103C. The cross-section of the shoulder 102 may be larger than the cross section of the spud 103.

Figure 5:
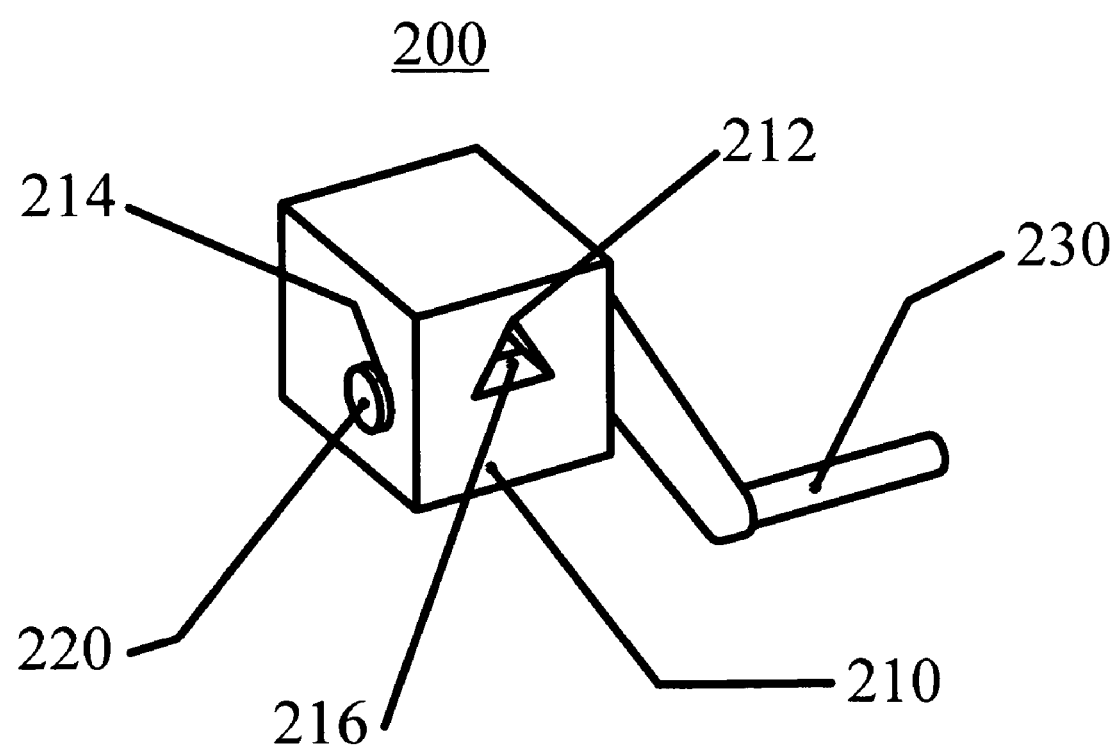
FIG. 5 illustrates a mandrel socket for the mill blank mandrel of FIG. 1.

FIG. 5 illustrates an embodiment of a mandrel socket 200. The mandrel socket 200 has a face 210 defining a mandrel socket opening 212. The mandrel socket 200 may also define a keyhole 214 through which a pin or key 220 may be inserted. The opening 212 and cavity 216 may have a general shape corresponding to the cross-section of the spud 103. The mandrel socket opening 212 defines a cavity 216 into which a spud 103 may be inserted. The cavity 216 may have a depth sufficient for the insertion of a spud 103 to be partially or fully inserted into the cavity 216. The depth of the cavity may be sufficient to allow the insertion of the spud 103 to the shoulder 102. The depth of the cavity 216 also may be sufficient so that the shoulder 102 of the mandrel 100 rests adjacent to or against the face 210 when the mill blank mandrel 100 is inserted thereto. The depth of the cavity 216 may define a bottom to which the face 105 of the spud 103 may rest when the spud 103 is inserted in the cavity 216.

Figure 6:
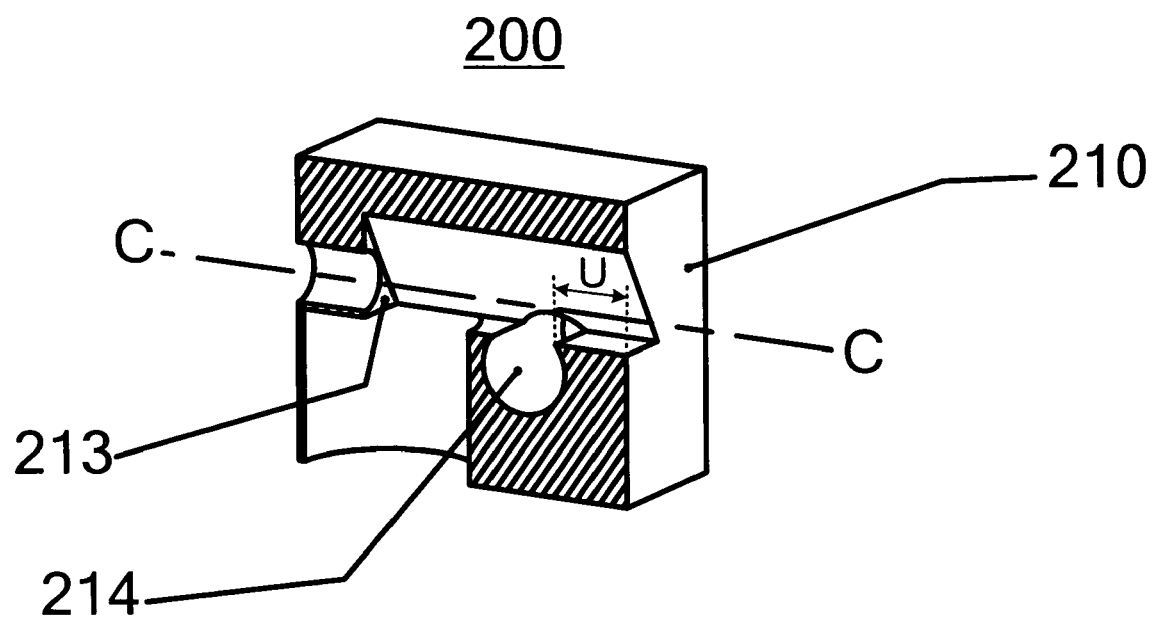
FIG. 6 illustrates a cut away view of the mandrel socket of FIG. 5 along longitudinal axis C-C of a cavity.
Figure 7:
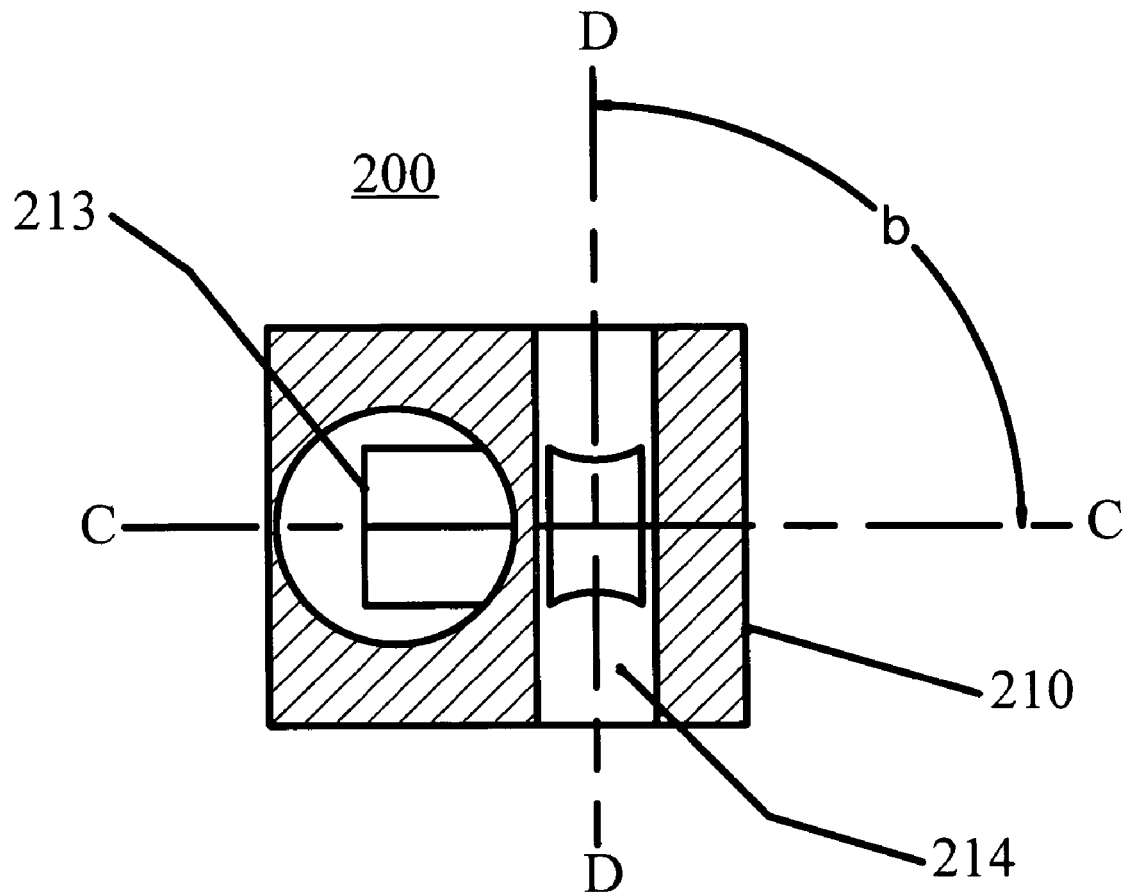
FIG. 7 illustrates a cut away view of the mandrel socket of FIG. 5 along longitudinal axis C-C and longitudinal axis D-D of a keyhole.

FIG. 6 illustrates a cross-section view of the mandrel socket 200 with through a longitudinal axis C-C of the cavity 216. FIG. 7 illustrates a cross-section view of the mandrel socket 200 through a longitudinal axis D-D of the key hole 214. The keyhole 214 may have a central axis D-D. The axis D-D may be at an angle b with respect to the axis C-C. The keyhole 214 may be positioned at axis D-D a distance u along axis C-C from the bottom 213 of the cavity 216. The keyhole 214 at axis D-D may also be positioned a distance from the central axis of the cavity C-C. The dimensions of the mandrel socket 200 correspond to the q, r, s, and t of the spud 103 respectively so that the keyhole 214 may align with the keyway 104 when the spud 103 is inserted into the cavity 216 to define a contiguous opening through the spud 103 and the mandrel socket 200.

The mandrel socket 201 may include a key or pin 220. The pin 220 may have a longitudinal axis collinear with the axis D-D of the keyhole 214. The pin 220 may be positioned by the keyhole 214. The pin 220 may have a handle 230 for manipulating or rotating the pin 220 within the keyhole 214. The pin may be manipulated between an open position and an engaged or locked position. The distance u may be slightly less than the distance t on spud 103 (FIG. 2) in order to create an interference fit with pin 220.

The pin 220 may have a linear or non-linear cross-section. The cross-section defines an outer surface of the pin 220 along the axis D-D. The cross-section of the pin 220 interfaces the keyway 104 in the spud 103. The cross-section of the pin 220 may allow the spud 103 to be inserted in the cavity 216 when the pin 220 is in the open position. The cross-section of the pin 220 may allow the pin and its outer surface to engage the spud 103 at the keyway 104 when the spud 103 is inserted in the cavity 216 and the pin is in the engaged position. By moving the pin 220 to the engaged position, the pin 220 may lock or rigidly secure the spud 103 in the cavity.

Figure 8:
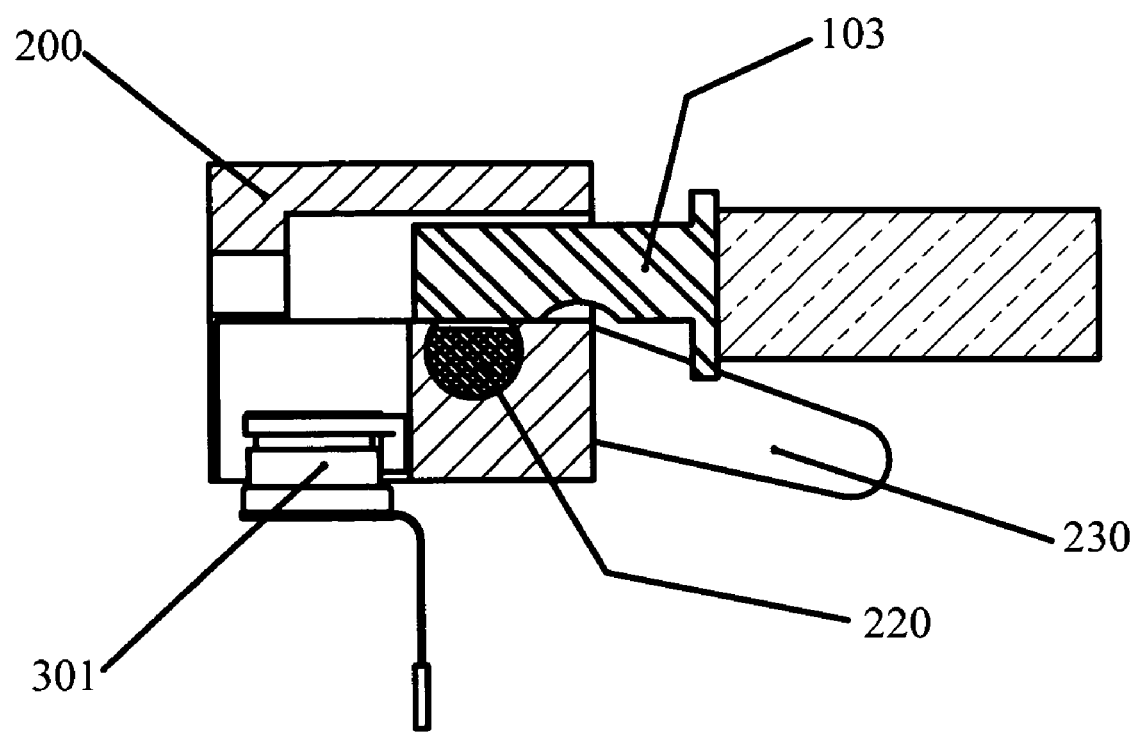
FIG. 8 illustrates a cut-away side view of the mandrel socket of FIG. 4 having a mill-blank mandrel of FIG. 1 partially engaged.

FIG. 8 illustrates a cut-away view of the mandrel socket with the spud 103 partially engaged within the cavity 216. The pin 220 is attached to a handle 230. In an embodiment, the handle may be rotated, thereby rotating the pin 220 through an angular motion about longitudinal axis D-D. The pin 220 may be rotated from an open position to a locked position. The pin 220 may have a D-shaped cross-section along at least a portion of the axis D-D where the pin coincides with the cavity 216. In an open position, a flat-portion of the D-Shaped cross-section is exposed to the cavity 216. The spud shaft 103 may enter and exit the cavity 216, thereby passing the flat portion of the pin 220 when the pin is in the open position.

Figure 9:
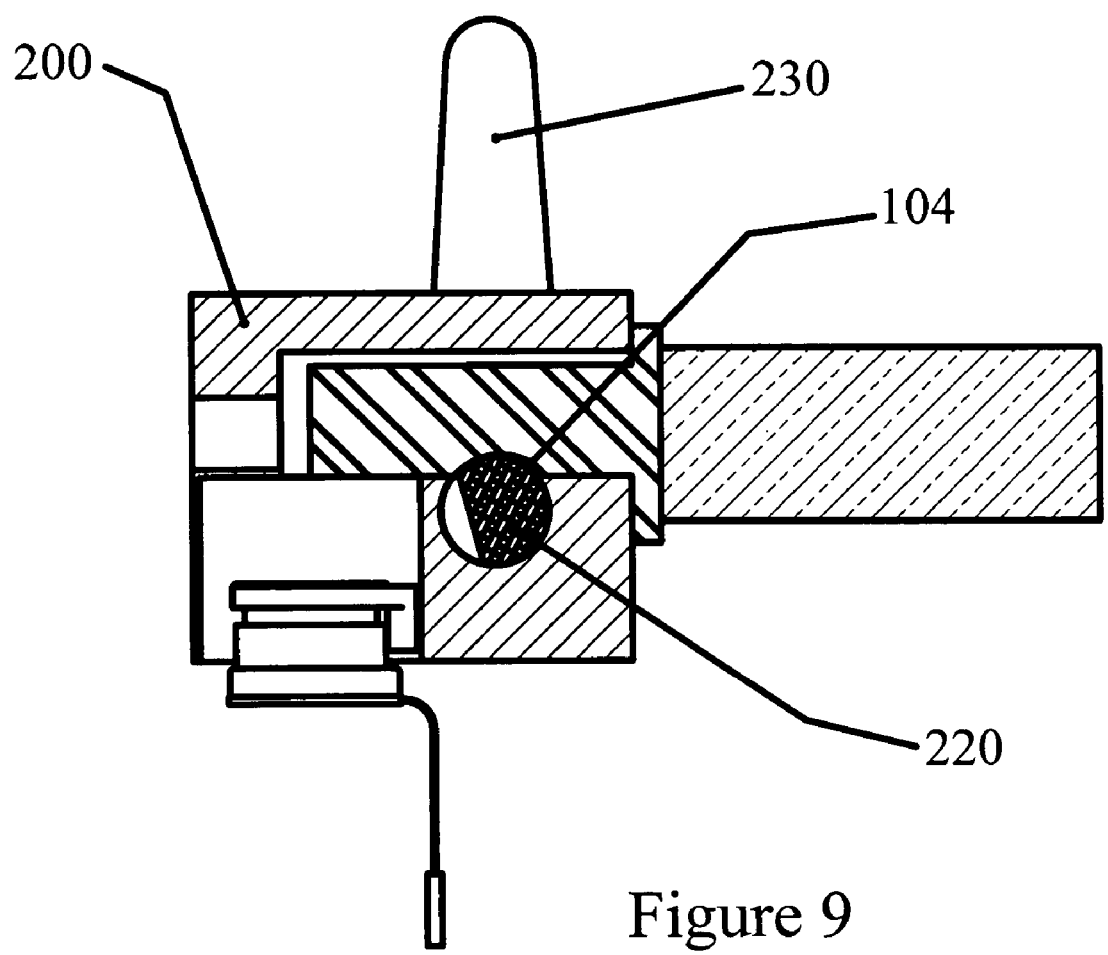
FIG. 9 illustrates a cut-away side view of the mandrel socket of FIG. 4 having mill-blank mandrel of FIG. 1 fully engaged.

FIG. 9 illustrates a cut away view of the mandrel socket 201 with the spud 103 engaged. The pin 220, having a D-Shaped cross-section has been rotated to a locked position. In an engaged or locked position, the pin 220 may engage the keyway 104 to create a friction connection at the interference between the pin 220 and the keyway 104 of the spud 103. The pin 220 may be rotated to apply a force or pressure against the spud 103 at the keyway 104. The force may rigidly secure the spud 103 into the cavity. The force may displace the spud 103 against an internal portion of the cavity opposite the pin, creating a friction connection between the spud 103 and the cavity 216 and the spud 103 and the pin 220. The pressure may lock the pin 220 within the cavity 216. The pin may be secured to resist lateral and rotational movement of the spud 103 with respect to the cavity 216 and therefore also with respect to the mandrel socket 200. The mandrel 100 may be substantially immobile and stabilized for a machining process.

A sensor 301 may be positioned within the mandrel socket 200. The sensor may detect the presence of the spud 103 within the cavity 216. The sensor 301 may detect the face 105 or other portion of the spud 103. The sensor 301 also may read markings or other identifiers on the spud 103. In an embodiment, the spud 103 may have a barcode marking at the face 105 of the spud 103. The sensor 301 may be a bar code reader that detects the spud within the cavity 216 and reads the barcode information on the spud 103. The barcode information may be used read from the spud 103 may be used to set-up, calibrate or establish a milling process for a milling machine. Similarly, the information may be used to verify that a proper spud is inserted in the cavity 216. The information may be checked against a database of information to verify that a proper mill blank mandrel 100 have been inserted in a mandrel socket 200. The sensor 301 may be any sensor capable of detecting the presence of the spud 103 within the cavity 216. The sensor also may be any sensor capable of reading information that may be provided on the spud. The sensor may be a position switch, a limit switch, an optical sensor, a bar code reader a RFID reader, an electromagnetic sensor, any combination thereof or the like.

Figure 10:
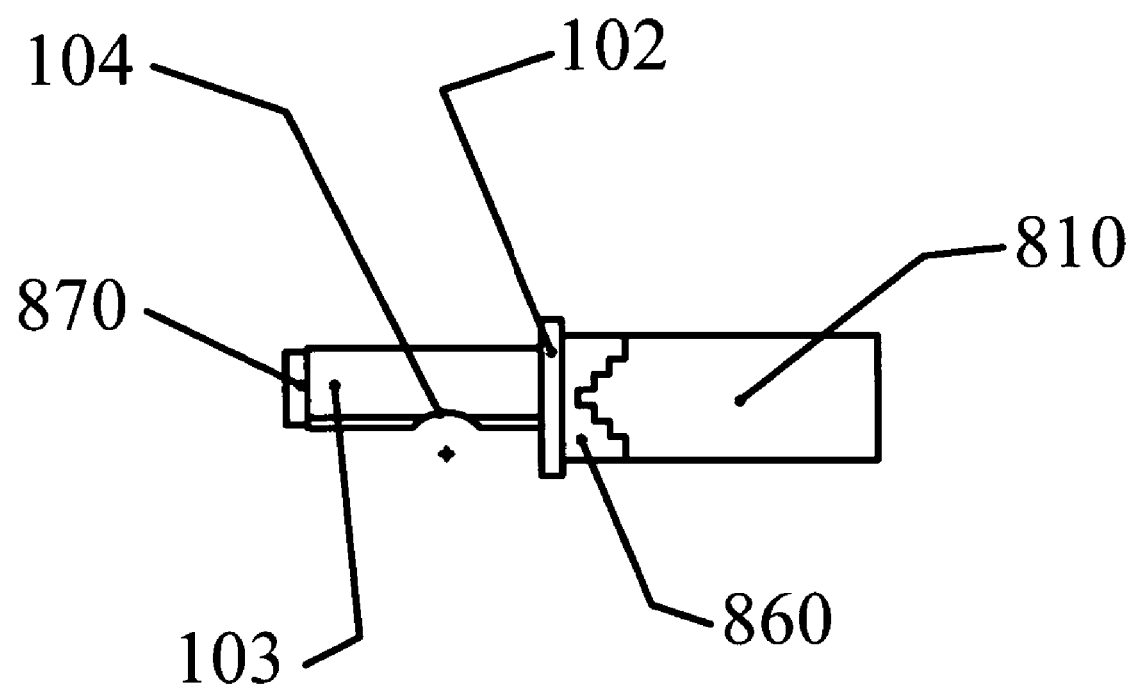
FIG. 10 illustrates an alternative embodiment of a mill blank mandrel.

FIG. 10 illustrates a RFID (radio frequency ID) chip 870 may be positioned on an end of the spud 103. A block of material 810 may be mechanically coupled to the mill blank mandrel 100. The RFID chip 870 may store information relating to the type, shape, size, arrangement, configuration of the material and any other information useful for identifying the spud mandrel 100. The RFID chip 870 may also include a code that may be read by a sensor 301 and used to unlock a milling machine. For example, the milling machine may have an interlock which prevents operation of the milling machine unless an appropriate mandrel is inserted in a mandrel socket. When the spud 103 is inserted in the cavity 216, the RFID may be read to determine the code stored thereon. The code may be used to unlock the milling machine, when it is determined that the code is valid. If no code is read or if the code is invalid, the milling machine may be inoperable.

The material 810 has a step-shaped end. The mandrel 100 includes a receiver 860 having a shape corresponding to the step-shaped end of the material 810. The interface between material and the receiver 860 may be coupled mechanically through a friction fit. The friction fit firmly and rigidly secures the material 810 to the mandrel 100 and supports the material 810 for a machining process.

Figure 11:
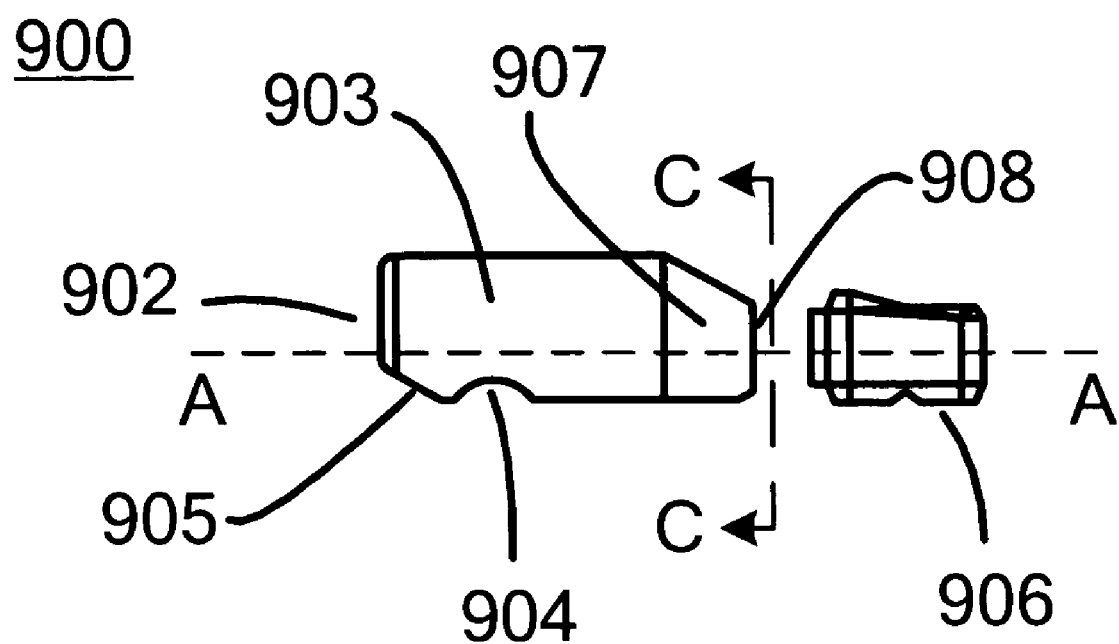
FIG. 11 illustrates a side view of an alternative embodiment of a mill blank mandrel.
Figure 12:
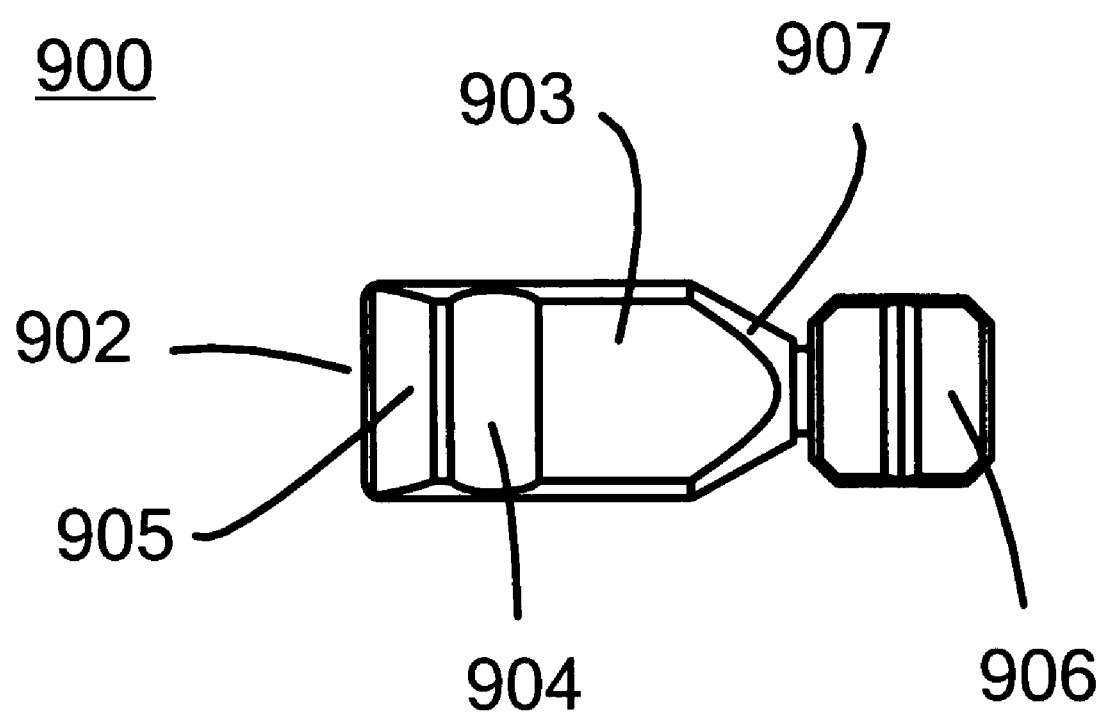
FIG. 12 illustrates a top view of the alternative embodiment of a mill blank mandrel of FIG. 11.

FIG. 11 and FIG. 12 illustrate the side and top views of an alternative embodiment of a mill blank mandrel respectively. The mill blank mandrel 900 includes an elongated body or shaft 903. In this embodiment, the mill blank mandrel may have a surface 902 at the opposite end of the mill blank mandrel from the machinable material 906 which may serve the same purpose as the shoulder 102 of the mill blank mandrel 103A of FIG. 4. The keyway 904 and the cross sectional shape of the spud 903 may be similar in purpose to the keyway 104 and the cross sectional shape of the spud 103 of the mill blank mandrel 103A of FIG. 4. The mill blank mandrel may be conically shaped with a surface 907 at the end of the mill blank mandrel closest to the machinable material 906. The conical surface 907 may be used to allow closer access of the cutting or grinding tool or bur to the machinable material 906, thereby reducing the amount of material wasted. The mandrel mill blank mandrel may include a keyway or groove 904. The purpose of the groove 904 may be similar to the purpose of the groove 104 of the mill blank mandrel 100 of FIG. 2. The cross sectional shape of the mill blank mandrel may be D shaped as in the spud 103 of FIG. 4, and serves the same purpose as the cross sectional shape of the spud 103 of FIG. 4. The block of machinable material 906 affixed to the spud may be generally shaped in such a fashion as to minimize material cutting time or excessive cutoff of a precious material. The block of machinable material 906 may be generally shaped like a dental restoration, such as a full crown.

Figure 13:
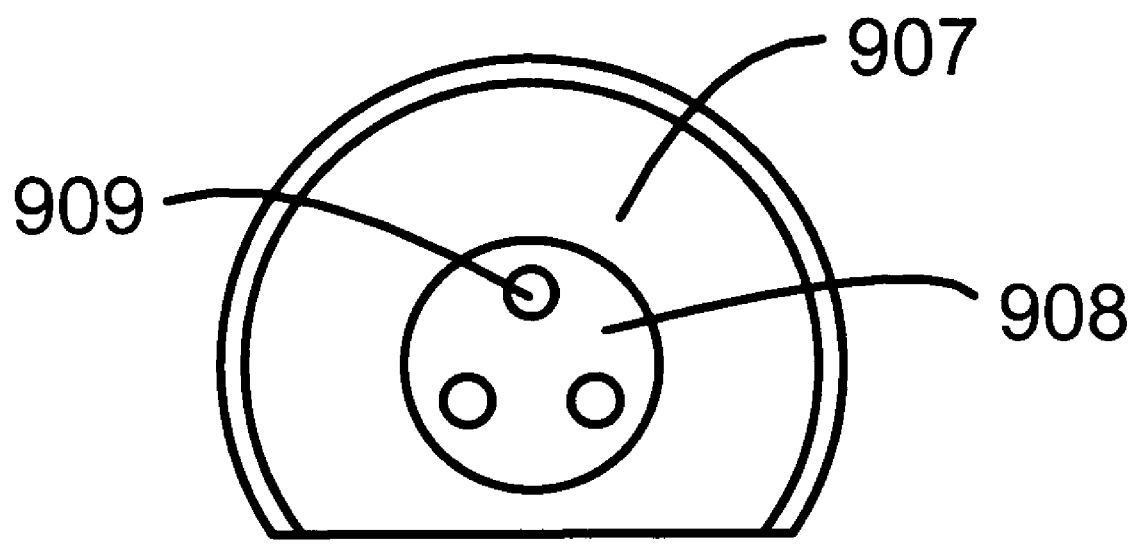
FIG. 13 illustrates an end view of the mill blank mandrel of FIG. 11, illustrating an epoxy gap.

FIG. 13 provides a side view of the mounting spud 903 of the mill blank mandrel of FIG. 11. The spud 903 has an end surface 907. To assist with the mounting of the blank, an indent 908 is provided with standoffs 909. The indent 908 accepts an epoxy or other fixative. The standoffs 909 maintain a correct and optimal gap between the end surface 907 of the mill blank mandrel, and the machinable material 906. Of course, the mandrel can have any appropriate cross section, including circular, non-circular, triangular and such.

Figure 14:
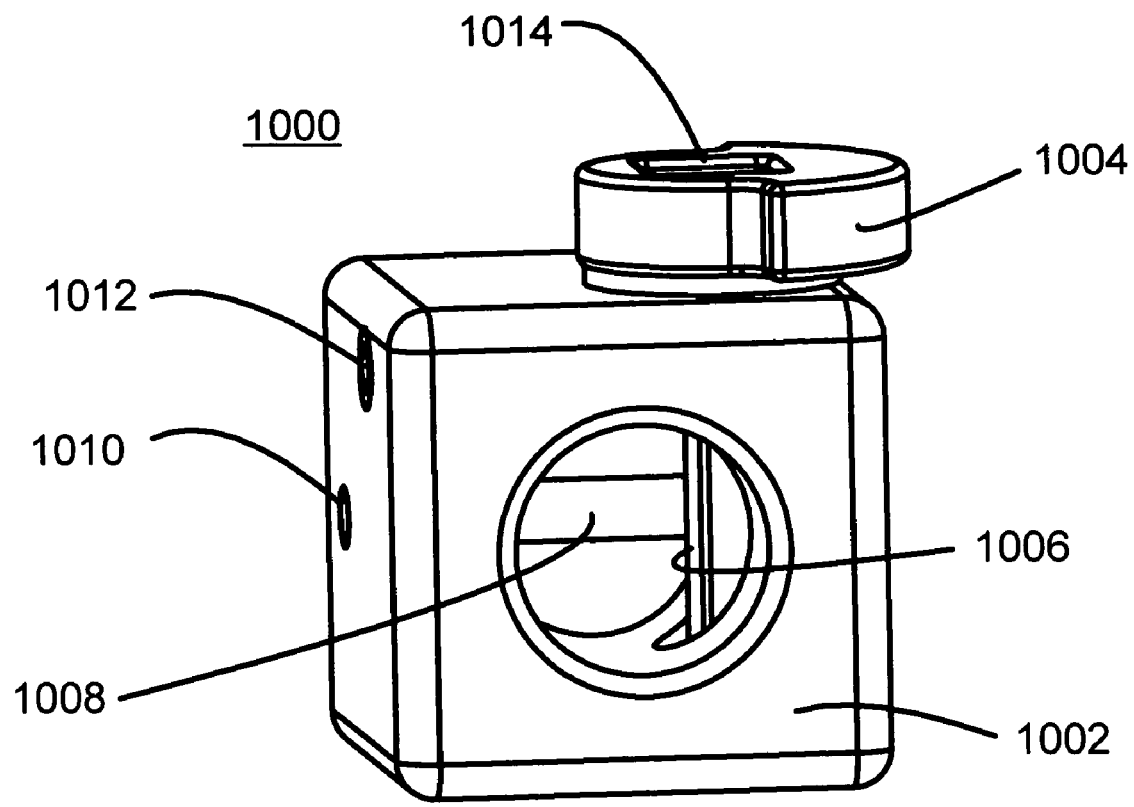
FIG. 14 provides a perspective view of the mandrel socket and cam for receiving the mill blank mandrel.

FIGS. 14, 15, 16 and 17 illustrate another embodiment of the mandrel mill socket, and specifically an embodiment that will work with the design of the mandrel shown in FIGS. 11, 12 and 13. The most notable difference with the mandrel is that it has no shoulder. Instead, it relies on its surface 902 to impact a travel limit in the mandrel socket. FIG. 14 provides a perspective of such a mandrel socket 1000. The mandrel socket 1000 has a frame 1002 having a central, generally cylindrical opening 1018 for accepting the elongated body of the mandrel mill blank. A pin 1008 acts as a travel limit to the insertion of the mandrel. While the opening is generally cylindrical in this illustration, it can match the cross-sectional shape of the mandrel.

Figure 15:
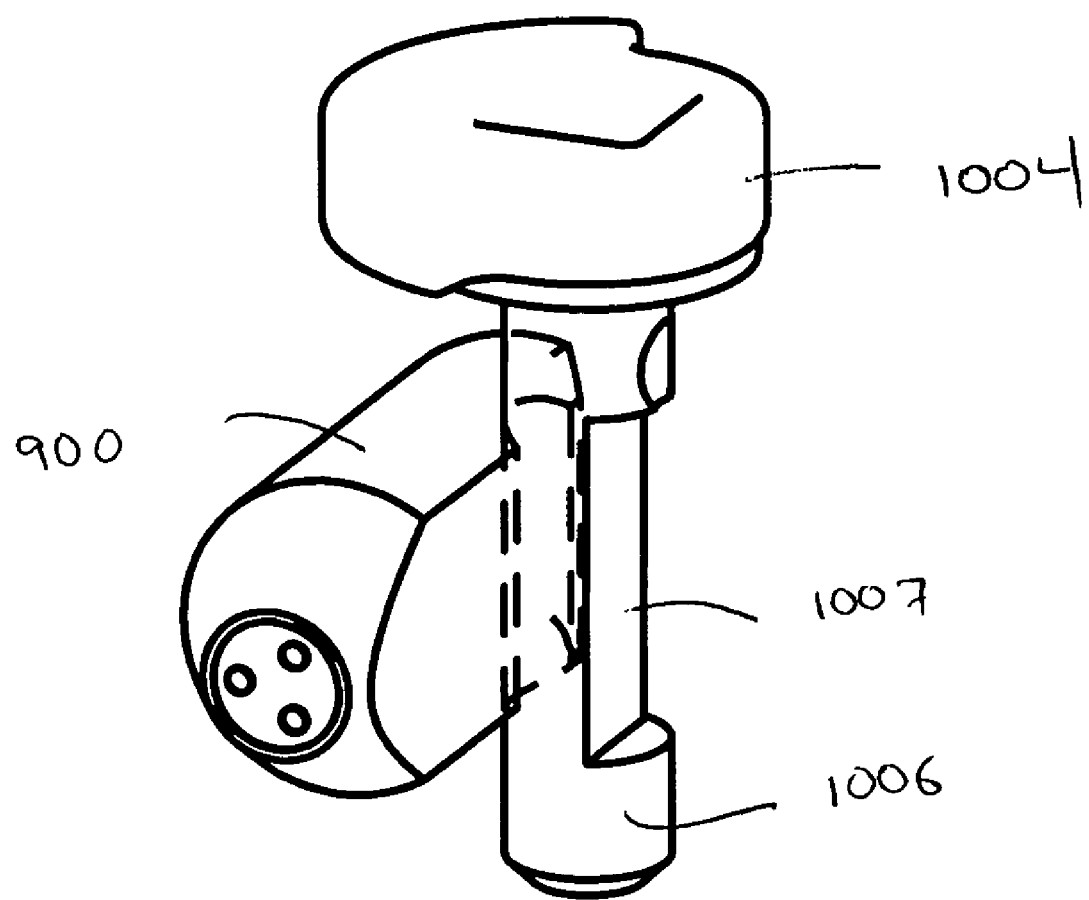
FIG. 15 illustrates the cam in an engaged position with the spud.
Figure 16:
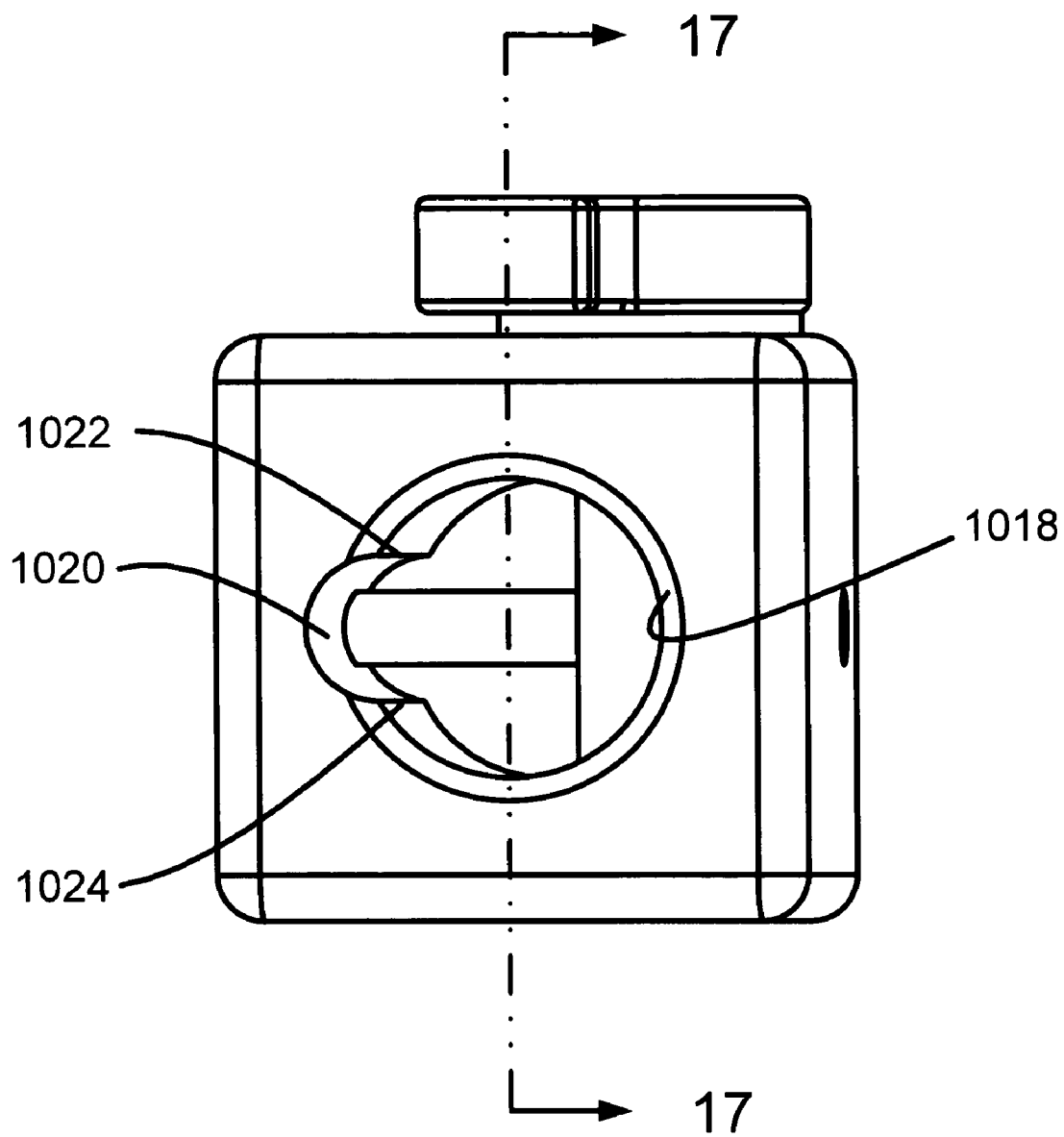
FIG. 16 shows an alternative version of the mandrel socket.

A cam 1004 is used to lock the mandrel and associated mill blank in place. Once inserted, the groove 904 on the mandrel is generally adjacent to the shaft 1006 of the cam 1004. The shaft 1006 has a reduced portion 1005. Thus, when the cam is in a first position, the reduced portion 1007 is adjacent to the mandrel, allowing for easier insertion. The cam 1004 is then rotated so that the reduced portion 1007 is no longer adjacent to the mandrel and the full radius portion engages the groove 904, as shown in FIG. 15. This creates a press fit and holds the mandrel securely. To prevent the inadvertent rotation of the cam, a set screw 1012 can be placed in the frame 1002. This set screw can load a spring and ball detent to prevent inadvertent rotation. A key 1014 on the top of the cam 1004 may be engaged to overcome the spring's resistance and rotate the cam into engagement with the mandrel.

The contact between the shaft of the mandrel and the mandrel socket can be enhanced by locating an additional curvature 1020 to the opening 1018. The intersection between the two curves creates contact lines 1022 and 1024. Thus, when the cam engages the mandrel, the outer surface of the mandrel is pressed into these contact lines.

Figure 17:
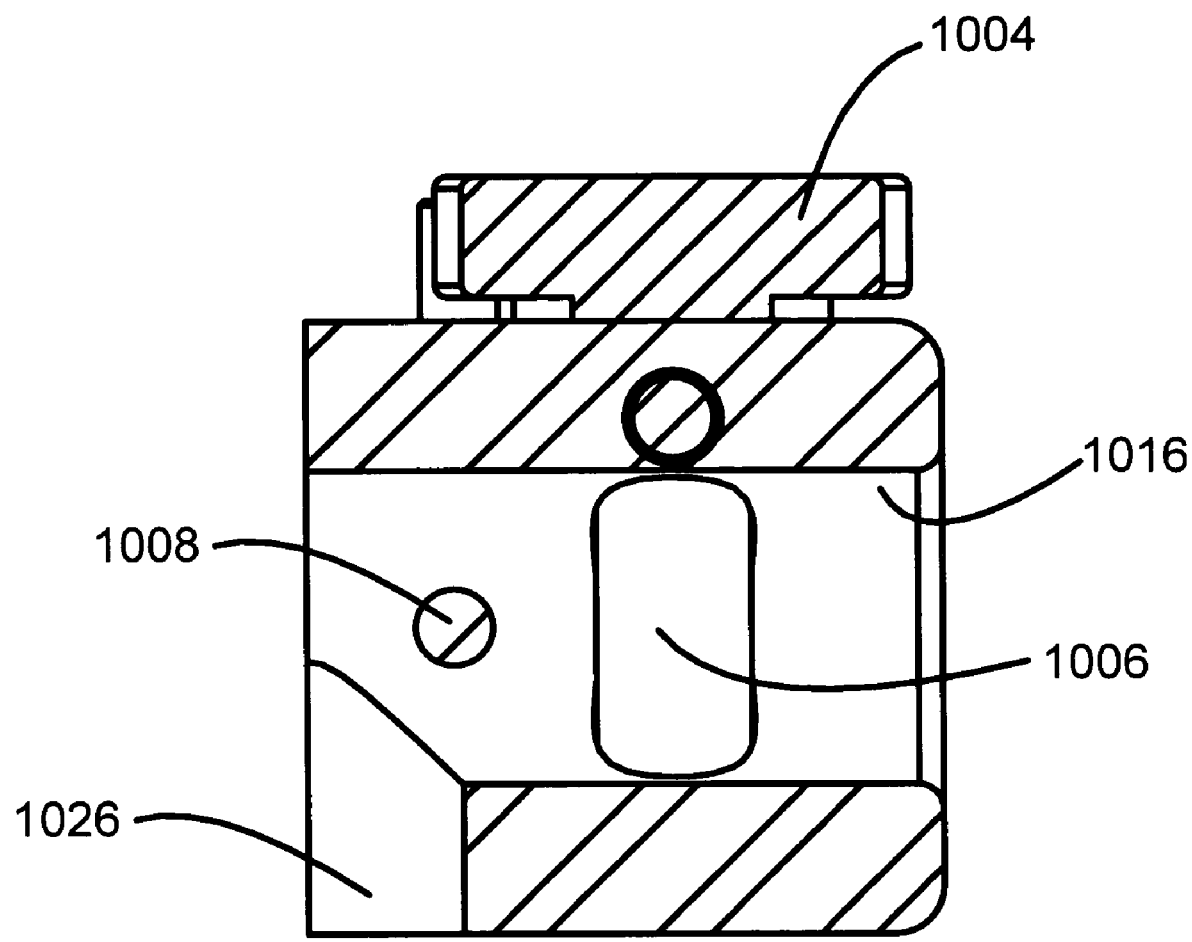
FIG. 17 is a sectional across the mandrel socket.

Finally, FIG. 17 provides a sectional view of the mandrel socket 1000. Of particular interest, the mandrel socket may have a drain portion 1026. This helps prevent material from cluttering the inside of the socket. For example, while the mill blank is being worked, filings are thrown off These filings and cooling water can contaminate the end surface of the mandrel. Thus, when the mandrel is being inserted or removed from the socket, these filings and fluid can accumulate in the socket. Drain 1026 provides a easy path to evacuate this clutter.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A mill blank mandrel system for securing a machinable dental blank within a dental milling machine, comprising:
   a mill blank mandrel comprising:
      an elongated shaft extending along a first longitudinal axis, the elongated shaft including a recess consisting of a fully-concave arcuate surface extending perpendicular to the first longitudinal axis, the cross-section of the elongated shaft being non-stepped along the first longitudinal axis except for the recess; and
      a shoulder extending from an end portion of the elongated shaft, the shoulder having an outer profile larger than an outer profile of the elongated shaft and having a surface for accepting the machinable dental blank;
   a mandrel socket comprising:
      a first elongated opening extending along a second longitudinal axis, the first elongated opening sized and shaped for receiving the elongated shaft of the mill blank mandrel; and
      a second opening in communication with the first opening and extending perpendicular to the second longitudinal axis, wherein the second opening is at least partially aligned with the recess in the elongated shaft of the mill blank mandrel to define a locking aperture when the elongated shaft of the mill blank mandrel is received within the first elongated opening of the mandrel socket; and
   a locking pin having a D-shaped cross section having a flat surface joined at opposite ends to a convexly-curved surface, the locking pin being positioned within the second opening of the mandrel socket, the locking pin connected to an actuator for moving the locking pin between a receiving position and a locked position, wherein in the receiving position the locking pin allows the elongated shaft of the mill blank mandrel to be inserted into the first elongated opening of the mandrel socket and wherein in the locked position the locking pin secures the elongated shaft of the mill blank mandrel within the first elongated opening of the mandrel socket via engagement of the convexly-curved surface of the locking pin with the arcuate surface of the recess of the elongated shaft.

2. The mill blank mandrel system of claim 1 further including the machinable blank attached to the elongated shaft.

3. The mill blank mandrel system of claim 2 wherein the machinable blank comprises a ceramic.

4. The mill blank mandrel system of claim 1 wherein in the receiving position the locking pin is positioned outside of the first elongated opening of the mandrel socket and wherein in the locked position the locking pin is at least partially positioned within the first elongated opening of the mandrel socket.

5. The mill blank mandrel system of claim 1, wherein the movement of the locking pin between the receiving position and the locked position is a rotational movement.

6. The mill blank mandrel system of claim 1 wherein in the receiving position the flat surface is positioned adjacent to the first elongated opening of the mandrel socket and wherein in the locked position the convexly-curved surface is at least partially positioned within the first elongated opening of the mandrel socket.

7. The mill blank mandrel system of claim 1, wherein the actuator is in the form of a handle.

8. The mill blank mandrel system of claim 1, wherein in the receiving position the flat surface of the locking pin is substantially coplanar with a flat surface of the mandrel socket.

9. The mill blank mandrel system of claim 1 further comprising a sensor for detecting when the elongated shaft of the mill blank mandrel is positioned within the first elongated opening of the mandrel socket.

10. The mill blank mandrel system of claim 1 further comprising a sensor for reading information associated with the mill blank mandrel.

11. The mill blank mandrel system of claim 10 wherein the sensor is an RFID reader and the information associated with the mill blank mandrel is stored on an RFID chip.

12. The mill blank mandrel system of claim 1 wherein the surface for accepting the machinable dental blank is configured for receiving a fixation material for securing the machinable dental blank to the mill blank mandrel.

13. The mill blank mandrel system of claim 1 wherein the shoulder and the machinable dental blank are a unitary part.

14. A mill blank mandrel system for securing a machinable dental blank within a dental milling machine, comprising:
- a mill blank mandrel comprising an elongated shaft extending along a first longitudinal axis, the elongated shaft including a concave recess consisting of a fully-concave arcuate surface extending perpendicular to the first longitudinal axis, the cross-section of the elongated shaft being non-stepped along the first longitudinal axis except for the recess, a first end portion of the elongated shaft comprising an engagement surface for engaging with the machinable dental blank and a shoulder extending radially outward from the elongated shaft for limiting travel of the mill blank mandrel within a mandrel socket;
- the mandrel socket comprising:
  - a first elongated opening extending along a second longitudinal axis, the first elongated opening sized and shaped for receiving the elongated shaft of the mill blank mandrel; and
  - a second opening in communication with the first opening and extending perpendicular to the second longitudinal axis, wherein the second opening is at least partially aligned with the concave recess in the elongated shaft of the mill blank mandrel when the elongated shaft of the mill blank mandrel is received within the first elongated opening of the mandrel socket; and
- a locking pin having a D-shaped cross section having a flat surface joined at opposite ends to a convexly-curved surface, the locking pin being positioned within the second opening of the mandrel socket, the locking pin connected to an actuator for rotating the locking pin between a receiving position and a locked position, wherein in the receiving position the locking pin allows the elongated shaft of the mill blank mandrel to be inserted into the first elongated opening of the mandrel socket and wherein in the locked position the locking pin secures the elongated shaft of the mill blank mandrel within the first elongated opening of the mandrel socket via engagement of the convexly-curved surface of the locking pin with the arcuate surface of the recess of the elongated shaft, wherein in the receiving position the locking pin is positioned outside of the first elongated opening of the mandrel socket and wherein in the locked position the locking pin is at least partially positioned within the first elongated opening of the mandrel socket.

15. The mill blank mandrel system of claim 14 wherein the movement of the locking pin between the receiving position and the locked position is a rotational movement.

16. The mill blank mandrel system of claim 14 wherein in the receiving position the flat surface is positioned adjacent to the first elongated opening of the mandrel socket and wherein in the locked positioned the convexly-curved surface is at least partially positioned within the first elongated opening of the mandrel socket.

17. The mill blank mandrel system of claim 14 wherein the actuator is in the form of a handle.

18. The mill blank mandrel system of claim 14 wherein in the receiving position the flat surface of the locking pin is substantially coplanar with a flat surface of the mandrel socket.

19. The mill blank mandrel system of claim 14 wherein the surface for accepting the machinable dental blank is configured for receiving a fixation material for securing the machinable dental blank to the mill blank mandrel.

20. The mill blank mandrel system of claim 14 wherein the shoulder and the machinable dental blank are a unitary part.

21. The mill blank mandrel system of claim 14 further comprising the machinable dental blank attached to the engagement surface of the elongated shaft.

* * * * *